United States Patent
Park et al.

(10) Patent No.: US 9,545,098 B2
(45) Date of Patent: Jan. 17, 2017

(54) INSECTICIDAL FEEDING BEADS, SYSTEMS COMPRISING THE BEADS, AND METHODS OF MAKING THE BEADS

(71) Applicant: Henkel Consumer Goods Inc., Scottsdale, AZ (US)

(72) Inventors: Debra A. Park, Mesa, AZ (US); Joan M. Bergstrom, Scottsdale, AZ (US); Arlana M. Brugato, Scottsdale, AZ (US)

(73) Assignee: Henkel Consumer Goods Inc., Scottsdale, AZ (US)

( * ) Notice: Subject to any disclaimer, the term of this patent is extended or adjusted under 35 U.S.C. 154(b) by 439 days.

(21) Appl. No.: 13/859,932

(22) Filed: Apr. 10, 2013

(65) Prior Publication Data

US 2014/0308327 A1    Oct. 16, 2014

(51) Int. Cl.
*A61K 9/14* (2006.01)
*A01N 25/00* (2006.01)
*A01N 25/10* (2006.01)

(52) U.S. Cl.
CPC .............. *A01N 25/006* (2013.01); *A01N 25/10* (2013.01)

(58) Field of Classification Search
CPC ........................... A01N 25/006; A01N 25/10
See application file for complete search history.

(56) References Cited

U.S. PATENT DOCUMENTS

| | | |
|---|---|---|
| 4,812,309 A | 3/1989 | Ong |
| 4,983,390 A | 1/1991 | Levy |
| 5,567,430 A | 10/1996 | Levy |
| 5,741,521 A | 4/1998 | Knight et al. |
| 2002/0098983 A1 | 7/2002 | Pursell et al. |
| 2009/0270349 A1 | 10/2009 | Murphy et al. |
| 2013/0195946 A1 | 8/2013 | Stamper et al. |

FOREIGN PATENT DOCUMENTS

| | | |
|---|---|---|
| EP | 0285404 A2 | 10/1988 |
| EP | 0953579 A2 | 11/1999 |
| EP | 0726028 B1 | 8/2001 |
| JP | H10291901 A | 11/1998 |
| JP | 2002-284608 A | 10/2002 |
| JP | 2004-099597 A | 4/2004 |
| WO | 89/12450 A1 | 12/1989 |
| WO | 89/12451 A1 | 12/1989 |
| WO | 02/089579 A1 | 11/2002 |
| WO | 02/090320 A2 | 11/2002 |
| WO | 02/090321 A1 | 11/2002 |
| WO | 2004/006677 A1 | 1/2004 |
| WO | 2004/020399 A1 | 3/2004 |
| WO | 2008/031870 A2 | 3/2008 |

OTHER PUBLICATIONS

PCT International Search Report (PCT/US2014/027296) dated Jan. 7, 2014.
European Search Report (14782667.1) dated Jul. 9, 2016.

*Primary Examiner* — Nannette Holloman
(74) *Attorney, Agent, or Firm* — P. Scott Smith

(57) ABSTRACT

An insecticidal feeding bead comprises: a food source comprising a swellable starch; an insecticide active; and greater than or equal to 60 weight percent water, wherein weight percent is based upon a total weight of the insecticidal feeding bead. A method of making an insecticidal feeding system comprises: forming an insecticidal feeding bead, comprising: a food source comprising a swellable starch; an insecticide active; and greater than or equal to 60 weight percent water, wherein weight percent is based upon a total weight of the insecticidal feeding bead; absorbing the insecticide active in the swellable starch; and absorbing the swellable starch in the water.

7 Claims, No Drawings

INSECTICIDAL FEEDING BEADS, SYSTEMS COMPRISING THE BEADS, AND METHODS OF MAKING THE BEADS

TECHNICAL FIELD

The present disclosure relates generally to insecticidal feeding beads, and more particularly to, insecticidal feeding beads comprising a food source, wherein the food source comprises a swellable starch, an insecticide active, and water.

BACKGROUND

Insecticide formulations in semisolid or solid gel form can be distributed in the environment and generally used in ways to control pests that may not be possible or practical with powdered or liquid insecticide compositions. For example, controlled release of insecticidal actives, such as a slow-time release, can be possible by formulating an insecticide active into a gel matrix.

Gelled ant baits generally achieve nest kill by providing a food source together with a slow-acting insecticidal active such that the ants or roaches feed and bring the actives back to the nest. Gelled baits are convenient because of the spill proof nature of a polymer gel matrix, making this physical form ideal for incorporation in plastic bait stations that necessarily have open access ports, and into syringes for safe consumer application.

Ants prefer to feed on sources of sugar water such as nectar and insect honeydew. Therefore, ants generally prefer liquid (e.g., water) based bait systems over other bait forms such as gels or solids. However, liquid baits spill easily and can leak and create untidiness in the environment in which they are located. Additionally, since ant nests or other pest nests, such as cockroach nests (e.g., American cockroaches) can be located in large areas in an outdoor environment (e.g., outside a home, office building, commercial building, in a park, etc.), there is a need to provide a liquid based system that does not spill or leak, as well as a need to provide a system that can be easily broadcast to increase the chance of interaction with pests in the environment. Thus, what is needed are forms of insecticidal baits, besides solid amorphous masses, which retain sufficient amounts of water and a food source to promote continuous and direct feeding by insects over extended periods of time.

Furthermore, other desirable features and characteristics of the insecticidal feeding beads disclosed herein will become apparent from the subsequent detailed description and the appended claims, taken in conjunction with the accompanying drawings and this background.

BRIEF SUMMARY

Disclosed herein, in various embodiments, are insecticidal feeding beads, methods for making the insecticidal feeding beads, and articles comprising the insecticidal feeding beads.

In an embodiment, an insecticidal feeding bead comprises: a food source comprising a swellable starch; an insecticide active; and greater than or equal to 60 weight percent water, wherein weight percent is based upon a total weight of the insecticidal feeding bead.

In an embodiment, a method of making an insecticidal feeding system comprises: forming an insecticidal feeding bead, comprising: a food source comprising a swellable starch; an insecticide active; and greater than or equal to 60 weight percent water, wherein weight percent is based upon a total weight of the insecticidal feeding bead; absorbing the insecticide active in the swellable starch; and absorbing the swellable starch in the water.

In an embodiment, a method of producing insecticidal feeding beads comprises: preparing an aqueous solution comprising an insecticide active, a food source comprising a swellable starch, and greater than or equal to 60 weight percent water, wherein weight percent is based upon a total weight of the aqueous solution; dissolving the insecticide active and the food source comprising a swellable starch in the water; forming the insecticidal feeding beads.

DETAILED DESCRIPTION

The following detailed description is merely exemplary in nature and is not intended to limit the insecticidal feeding beads disclosed herein or the application and uses of the insecticidal feeding beads. Furthermore, there is no intention to be bound by any theory presented in the preceding background or the following detailed description.

Disclosed herein are insecticidal feeding beads, methods of making the insecticidal feeding beads, and systems formed from the insecticidal feeding beads. The insecticidal feeding beads disclosed herein can advantageously comprise a food source comprising a swellable starch, an insecticide active, and a liquid, e.g., greater than or equal to 60 weight percent (wt. %) water, oil, honey, or a combination comprising at least one of the foregoing, wherein weight percent is based upon a total weight of the insecticidal feeding bead. The swellable starch can advantageously be a naturally based material, which can be safer for the environment than other food sources generally used in insect bait systems. The insecticidal feeding beads disclosed herein comprising a food source, wherein the food source comprises a swellable starch, can absorb the insecticidal active and liquid present to form the insecticidal feeding bead. The insecticidal feeding beads formed can be broadcast (e.g., spread) to an environment (e.g., an outside environment including, but not limited to, outside a home, office, commercial building; park, etc.) and/or can be incorporated in a bait system for distribution in any environment (e.g., inside a home, office, commercial building and/or outside a home, office, commercial building, etc.).

The insecticidal feeding beads disclosed herein comprising a food source comprising a swellable starch can offer a solution to the problems associated with liquid bait materials, i.e., easily spilled, since the swellable starch can absorb the liquid and insecticide active used in the formation of the insecticidal feeding beads. The resulting insecticidal feeding beads can provide a form of insect or pest control that is attractive to the pests (e.g., ants, cockroaches (American cockroaches, outdoor cockroaches), crickets, silverfish, firebrats, earwigs) it is intended to eradicate. The insecticidal feeding beads can also provide a form of insect or pest control that is attractive to the consumer since it can be generally safer to handle and can generally be safer for the environment than other bait systems, since the insecticide active is absorbed by the naturally occurring swellable starch, leaving only the insecticidal feeding bead in the environment in which it will be used. Moreover, since the insecticidal feeding beads are not in a liquid form, there is less risk of exposure to the insecticide active to the end user of the insecticidal feeding beads.

As previously described, the food source can comprise a swellable starch. Starch as used herein generally refers to a naturally abundant carbohydrate found mainly in the seeds, fruits, tubers, roots, and stem pith of plants, e.g., in corn, potatoes, wheat, rice, and varying widely in appearance according to the source from which it is derived. Swellable starch as described herein generally refers to a starch with the ability to absorb greater than or equal to 1 times its volume in a liquid (e.g., water), specifically, greater than or equal to 2 times, more specifically, greater than or equal to 3 times, even more specifically, greater than or equal to 4 times, and still more specifically, greater than or equal to 5 times its volume in a liquid. The ability of the swellable starch to absorb liquid allows the insecticide active and liquid present in the insecticidal feeding beads disclosed herein to be available to the insect, but in a form that can be easier to transport and broadcast and less likely to release the insecticide active to the surrounding environment.

The swellable starch can comprise, for example, tapioca. Tapioca can generally be described as a starch extracted from cassava. Once extracted, the starch can be processed into several forms such as pre-cooked fine or coarse flakes, rectangular sticks, and spherical pearls. The pearls can have a diameter of about 1 millimeter (mm) to about 8 mm, specifically, 2 mm to 3 mm. The various forms of tapioca are generally soaked before cooking in order to rehydrate them. For example, tapioca in any of the forms disclosed herein can absorb greater than or equal to two times their volume in liquid. After cooking, the tapioca can be any desired color, including, but not limited to, transparent (e.g., allowing greater than or equal to 5% of visible light to transfer through it), white, brown, or pastel colors. Before cooking, tapioca is generally opaque (e.g., allowing less than or equal to 1% of visible light to transfer through it) and becomes translucent (e.g., allowing greater than 1% but less than 5% of visible light to pass through it) when cooked. Pearl tapioca is also known as boba in some cultures. It can be produced by passing the moist starch through a sieve under pressure.

The food source can, optionally, in addition to the swellable starch, comprise an additional bait to attract insects (e.g., crawling and/or flying insects). For example, the food source can additionally, optionally, further comprise sugars (e.g., small molecular weight sugars), moderate molecular weight oligosaccharides, larger molecular weight carbohydrates, grain foods, lipids, fats, hydrogenated fats, or animal or vegetable proteins, or mixtures of these various foods depending upon the targeted insects and the desired physical form of the finished bait. If sugar is used, it can comprise any mono- or disaccharide, any type of reduced sugar (sugar alcohols), derivatives of sugars (e.g., sugar amines) or polyhydroxy alcohols, molasses, and/or any of the known sugar syrups and jams. Foods in insect baits can include, but are not limited to, glucose, fructose, sucrose, dextrose, maltose, lactose, galactose, arabinose, glycerin, invert sugar, molasses, high fructose corn syrup, maple syrup, honey, hydrogenated vegetable shortening, black sugar, brown sugar, glucosamine, vegetable oil, and combinations comprising at least one of the foregoing.

The food source, when present, can be present in the insecticidal feeding beads in an amount of about 1 wt. % to about 70 wt. %, specifically, about 10 wt. % to about 60 wt. %, based on the total weight of the insecticidal feeding bead composition.

The insecticide active disclosed herein can be limitless. For example, the insecticidal feeding beads disclosed herein can be used to eradicate and/or control any type of crawling or flying pests. Additionally, even if the insecticide active is not readily soluble in water, it can be emulsified into water with one or more emulsifiers and/or one or more solvents to produce an emulsion that can be used subsequently to hydrate the food source. Exemplary insecticide actives can include, but are not limited to, Bacillus (e.g., Bacillus thuringiensis); Bacillus endotoxins (e.g., Bacillus thuringiensis delta-endotoxin); carbamates; chitin synthesis inhibitors; cholinesterase inhibitors; cyclodiene insecticides; ecdysone agonists; GABA-regulated chloride channel blockers; GABA antagonists; juvenile hormone mimics; macrocyclic lactones, lipid biosynthesis inhibitors; mitochondrial electron transport inhibitors (METI); molting inhibitors; naturally occurring or a genetically modified viral insecticide; neonicotinoids; nereisotoxin analogs; neuronal sodium channel blockers; nicotinic receptor agonists/antagonists compounds; octopamine receptor ligands; oxidative phosphorylation inhibitor compounds; pyrethroids; ryanodine receptor ligands; sodium channel modulators; uncoupler compounds; ureas; as well as combinations comprising at least one of the foregoing.

A number of exemplary insecticide actives can be useful for inclusion within the insecticidal feeding beads disclosed herein. These insecticides include, but are not limited to, (1) Organo(thio)phosphates: acephate, azamethiphos, azinphosmethyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon; (2) Carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate; (3) Pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin; (4) Growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen; (5) Nicotinic receptor agonists/antagonists compounds: clothianidin, dinotefuran, imidacloprid, thiamethoxam, nitenpyram, acetamiprid, thiacloprid; (6) GABA antagonist compounds: acetoprole, endosulfan, ethiprole, fipronil, vaniliprole; (7) Macrocyclic lactone insecticides: abamectin, emamectin, milbemectin, lepimectin, spinosad; (8) METI (mitochondrial electron transport inhibitor) I acaricides: fenazaquin, pyridaben, tebufenpyrad, tolfenpyrad; (9) METI II and III compounds: acequinocyl, fluacyprim, hydramethylnon; (10) Uncoupler compounds: chlorfenapyr; (11) Oxidative phosphorylation inhibitor compounds: cyhexatin, diafenthiuron, fenbutatin oxide, propargite; (12) Molting disruptor compounds: cryomazine; (13) Mixed function oxidase inhibitor compounds: piperonyl butoxide; (14) Sodium channel blocker compounds: indoxacarb, metaflumizone; (15) Miscellaneous insecticides: boric acid, sodium tetraborate pentahydrate (borax), benclothiaz, bifenazate, cartap, flonicamid, pyridalyl, pymetrozine, sulfur, thiocyclam, and malononitrile compounds as described in JP 2002 284608, WO 02/89579, WO 02/90320, WO 02/90321, WO 04/06677, WO 04/20399, or JP 2004 99597; and mixtures thereof.

More exemplary insecticide actives for use herein can include, but are not limited to, abamectin, acephate, acetamiprid, acetoprole, amidoflumet, avermectin, azadirachtin, azinphos-methyl, bifenthrin, bifenazate, bistrifluoron, boric acid, buprofezin, carbofuran, cartap, chlorfenapyr, chlorfluazuron, chlorpyrifos, chlorpyrifos-methyl, chromafenozide, clothianidin, cyflumetofen, cyfluthrin, beta-cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, esfenvalerate, ethiprole, fenothiocarb, fenoxycarb, fenpropathrin, fenvalerate, fipronil, flonicamid, flubendiamide, flucythrinate, tau-fluvalinate, flufenerim, flufenoxuron, fonophos, gamma-cyhalothrin, halofenozide, hexaflumuron, hydramethylnon, imidacloprid, indoxacarb, isofenphos, lufenuron, malathion, metaflumizone, metaldehyde, methamidophos, methidathion, methomyl, methoprene, methoxychlor, methoxyfenozide, metofluthrin, monocrotophos, nitenpyram, nithiazine, novaluron, noviflumuron, oxamyl, parathion, parathion-methyl, permethrin, phorate, phosalone, phosmet, phosphamidon, pirimicarb, profenofos, profluthrin, protrifenbute, pymetrozine, pyrafluprole, pyrethrin, pyridalyl, pyrifluquinazon, pyriprole, pyriproxyfen, rotenone, ryanodine, S1812 (Valent), sodium tetraborate pentahydrate (borax), spinosad, spiridiclofen, spiromesifen, spirotetramat, sulprofos, tebufenozide, teflubenzuron, tefluthrin, terbufos, tetrachlorvinphos, thiacloprid, thiamethoxam, thiodicarb, thiosultapsodium, tolfenpyrad, tralomethrin, triazamate, trichlorfon, triflumuron, aldicarb, imicyafos, fenamiphos, amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben, tebufenpyrad, *Bacillus thuringiensis* aizawai, *Bacillus thuringiensis* kurstaki, *Bacillus thuringiensis* delta endotoxin, baculovirus, entomopathogenic bacteria, entomopathogenic virus, entomopathogenic fungi, and mixtures thereof.

The total amount of insecticidal active used in the insecticidal feeding spheres disclosed herein can depend upon the targeted pests and their environment, the nature of the pesticide active, whether or not a mixture of actives is used, and if there is a synergistic enhancement of insecticidal activity when using combinations of actives. Generally, any of the above mentioned active(s) can be incorporated into the insecticidal feeding beads disclosed herein in trace amounts (e.g., about 0.0001 wt. % or less) to about 5 wt. %, based on the total weight of the beads (food source, water, and insecticide active). For example, the insecticidal active can be present in an amount of less than about 0.1 wt. %, unless the active is an inorganic substance such as boric acid or borax. For example, dinotefuran can be used in an amount of about 0.01 to about 0.10 wt. %; chlorfenapyr in an amount of about 0.01 to about 0.10 wt. %; spinosad in an amount of about 0.01 to about 0.05 wt. %; indoxacarb in an amount of about 0.01 to about 0.10 wt. %; avermectin in an amount of about 0.005 to about 0.02 wt. %; fipronil in an amount of about 0.0001 to about 0.01 wt. %; hydramethylnon in an amount of about 0.10 to about 0.30 wt. %, or boric acid or borax in an amount of about 0.50 to about 5.0 wt. %, or mixtures of any of these substances in any combination.

As previously described herein, the insecticidal feeding beads can comprise a liquid. For example, the insecticidal feeing beads can comprise greater than or equal to 50 wt. % water, specifically, greater than or equal to 60 wt. % water, more specifically, greater than or equal to 70% water, and even more specifically, greater than or equal to 80% water. The food source comprising a swellable starch can absorb the water to make the insecticidal feeding bead.

Methods of making the insecticidal feeding beads disclosed herein are also contemplated. For example, a method of producing the insecticidal feeding beads can comprise preparing an aqueous solution, wherein the aqueous solution comprises an insecticide active, a food source, and a liquid, dissolving the insecticide active and the food source in the liquid, and forming insecticidal feeding beads. The food source can comprise a swellable starch and the liquid can comprise water. The water can be present in an amount of greater than or equal to 50 wt. %, specifically, greater than or equal to 60 wt. %, wherein wt. % is based upon a total weight of the aqueous solution. A plurality of the insecticidal feeding beads can then be placed in a bait station or a plurality of the insecticidal feeding beads can be broadcast to an area. The swellable starch used in making the insecticidal feeding beads can comprise a tapioca bead.

Methods of making an insecticidal feeding system utilizing the insecticidal feeding beads disclosed herein are also contemplated. For example, a method of making an insecticidal feeding system can comprise forming an insecticidal feeding bead, absorbing the insecticide active in the swellable starch, and absorbing the swellable starch in the water to form the insecticidal feeding system. The insecticidal feeding bead can comprise a food source comprising a swellable starch, an insecticide active, and greater than or equal to 60 wt. % water, wherein wt. % is based upon a total weight of the insecticidal feeding bead. The insecticidal feeding beads can then be placed in a bait station or broadcast to an area. The swellable starch used in making the insecticidal feeding beads can comprise a tapioca bead.

The insecticidal feeding beads disclosed herein can provide an attractive pest solution in terms of safety to the consumer and safety to the environment, since the insecticide active is enclose within the insecticidal feeding beads. Additionally, the insecticidal feeding beads disclosed herein comprising a food source comprising a swellable starch can offer a solution to the problems associated with liquid bait materials, i.e., easily spilled, since the swellable starch can absorb the liquid and insecticide active used in the formation of the insecticidal feeding beads.

In an embodiment, an insecticidal feeding bead comprises: a food source comprising a swellable starch; an insecticide active; and greater than or equal to 60 weight percent water, wherein weight percent is based upon a total weight of the insecticidal feeding bead.

In an embodiment, a method of making an insecticidal feeding system comprises: forming an insecticidal feeding bead, comprising: a food source comprising a swellable starch; an insecticide active; and greater than or equal to 60 weight percent water, wherein weight percent is based upon a total weight of the insecticidal feeding bead; absorbing the insecticide active in the swellable starch; and absorbing the swellable starch in the water.

In an embodiment, a method of producing insecticidal feeding beads comprises: preparing an aqueous solution comprising an insecticide active, a food source comprising a swellable starch, and greater than or equal to 60 weight percent water, wherein weight percent is based upon a total weight of the aqueous solution; dissolving the insecticide active and the food source comprising a swellable starch in the water; forming the insecticidal feeding beads.

In the various embodiments, (i) the swellable starch comprises a tapioca bead; and/or (ii) the swellable starch has a volume and wherein the swellable starch absorbs greater than or equal to two times the volume in water; and/or (iii) the swellable starch has a diameter of 1 millimeter to 8 millimeters; and/or (iv) the diameter is 2 millimeters to 3 millimeters; and/or (v) the food source further comprises a source selected from the group consisting of sugars, sugar derivatives, polyhydroxy alcohols, syrups, oligosaccharides, carbohydrates, grain foods, lipids, fats, hydrogenated fats, animal protein, vegetable proteins, or a combination comprising at least one of the foregoing; and/or (vi) the source is selected from the group consisting of glucose, fructose, sucrose, dextrose, maltose, lactose, galactose, arabinose, glycerin, invert sugar, molasses, high fructose corn syrup, honey, hydrogenated vegetable shortening, black sugar, brown sugar, glucosamine, or a combination comprising at least one of the foregoing.

In the various embodiments, the method further comprises (i) placing a plurality of the insecticidal feeding beads in a bait station; and/or (ii) broadcasting a plurality of the insecticidal feeding beads to an area; and/or (iii) absorbing greater than or equal to two times a volume of the swellable starch in the water.

All ranges disclosed herein are inclusive of the endpoints, and the endpoints are independently combinable with each other (e.g., ranges of "up to 25 wt. %, or, more specifically, 5 wt. % to 20 wt. %", is inclusive of the endpoints and all intermediate values of the ranges of "5 wt. % to 25 wt. %," etc.). "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the film(s) includes one or more films) Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment, it being understood that various changes may be made in the function and arrangement of elements described in an exemplary embodiment without departing from the scope of the invention as set forth in the appended claims and their legal equivalents.

What is claimed is:

1. An insecticidal feeding bead, comprising:
   a food source comprising a swellable starch;
   0.0001 wt % to 5 wt % of an insecticide active; and
   greater than or equal to 70 weight percent water, wherein weight percent is based upon a total weight of the insecticidal feeding bead.

2. The insecticidal feeding bead of claim 1, wherein the swellable starch comprises a tapioca bead.

3. The insecticidal feeding bead of claim 1, wherein the swellable starch has a volume and wherein the swellable starch absorbs greater than or equal to two times the volume in water.

4. The insecticidal feeding bead of claim 1, wherein the swellable starch has a diameter of 1 millimeter to 8 millimeters.

5. The insecticidal feeding bead of claim 4, wherein the diameter is 2 millimeters to 3 millimeters.

6. The insecticidal feeding bead of claim 1, wherein the food source further comprises a source selected from the group consisting of sugars, sugar derivatives, polyhydroxy alcohols, syrups, oligosaccharides, carbohydrates, grain foods, lipids, fats, hydrogenated fats, animal protein, vegetable proteins, or a combination comprising at least one of the foregoing.

7. The insecticidal feeding bead of claim 6, wherein the source is selected from the group consisting of glucose, fructose, sucrose, dextrose, maltose, lactose, galactose, arabinose, glycerin, invert sugar, molasses, high fructose corn syrup, honey, hydrogenated vegetable shortening, black sugar, brown sugar, glucosamine, or a combination comprising at least one of the foregoing.

* * * * *